United States Patent [19]

Waditschatka

[11] Patent Number: 5,276,186

[45] Date of Patent: Jan. 4, 1994

[54] PROCESS FOR THE PRODUCTION OF GUANIDINE DERIVATIVES

[75] Inventor: Rudolf Waditschatka, Gipf-Oberfrick, Switzerland

[73] Assignee: Ciba-Geigy Corporation, Ardsley, N.Y.

[21] Appl. No.: 981,683

[22] Filed: Nov. 25, 1992

Related U.S. Application Data

[63] Continuation-in-part of Ser. No. 849,555, Mar. 11, 1992, abandoned.

[51] Int. Cl.$^5$ ............................................. C07C 277/02
[52] U.S. Cl. ...................................................... 564/238
[58] Field of Search ........................................ 564/238

[56] References Cited

U.S. PATENT DOCUMENTS

| | | | |
|---|---|---|---|
| 2,615,045 | 10/1952 | Kaiser et al. | 260/565 |
| 3,976,643 | 8/1976 | Diamond et al. | 564/238 |
| 4,906,778 | 3/1990 | Schaffhausen | 564/227 |

FOREIGN PATENT DOCUMENTS

| | | |
|---|---|---|
| 0164204 | 12/1985 | European Pat. Off. |
| 1241151 | 7/1959 | France |
| 1514907 | 6/1978 | United Kingdom |

OTHER PUBLICATIONS

McKee, R., "On the Oxygen Ethers of the Ureas, etc." *Amer. Chem. J.*, 26, No. 3, p. 221 (1901).
Kampf, A., "Uber Darstellung Aromatisch Substituirter Guanidine Aus Cyanamide," *Chem. Ber.* (37), pp. 1681-1684 (1904).
Houben—Weyl, 8, pp. 180-181 (1952).
Weiss, Corporate Brochure, p. 97 (1978) SKW Trostberg Ag.
M. G. Ivanov, "Kinetics and mechanism" pp. 681-684. *Kinetika i Kataliz,* vol. 9, No. 3 (1968).
Journal of the American Chemical Society, Vol. 51, pp. 476-479, GBL Smith (1929).

*Primary Examiner*—Glennon H. Hollrah
*Assistant Examiner*—P. O'Sullivan
*Attorney, Agent, or Firm*—Marla J. Mathias; Kevin T. Mansfield

[57] ABSTRACT

A process for the production of phenylguanidine carbonate and hydrogencarbonate by reacting aqueous cyanamide with aniline hydrochloride within a specified pH range, combining the reaction mixture with an alkali metal carbonate or hydrogencarbonate, and separating the crystalline product.

12 Claims, No Drawings

PROCESS FOR THE PRODUCTION OF GUANIDINE DERIVATIVES

This is a continuation-in-part of application Ser. No. 07/849,555 filed Mar. 11, 1992, now abandoned.

The present invention relates to an improved process for the production of phenylguanidine carbonate and hydrogencarbonate by reacting aqueous cynamide with aniline hydrochloride within a specified pH range, combining the reaction mixture with an alkali metal carbonate or hydrogencarbonate, and separating the crystalline product.

Phenylguanidine carbonate is used in the preparation of pharmaceutically active pyrimidines, as described in European patent application EP-A-0 164 204, and phenylguanidine hydrogencarbonate is used as an intermediate in the production of pesticidally active pyrimidine derivatives, as described in U.S. Pat. No. 4,931,560.

A synthesis of phenylguanidine hydrogencarbonate is described by the firm SKW Trostberg AG on page 97 of a corporate brochure from 1978. This process has the disadvantages that a large quantity of waste water is produced, the yield is relatively low, and side products are produced, e.g. phenylurea and diphenylurea. Furthermore, activated carbon is added during the reaction which must be separated off very carefully. The Trostberg reference is silent on a process for the production of phenylguanidine carbonate.

The synthesis of phenylguanidine from cyanamide and aniline hydrochloride is known, and described, for example, in Am. Chem. Journal, vol. 26, no. 3, p. 221 (1901). The synthesis of aromatic substituted guanidines from cyanamide is described by A. Kampf, Chem. Ber. vol. 37, p. 1681–4 (1904). Further synthesis of substituted guanidines are described, for example, in Houben-Weyl, Vol. 8, p. 180–1 (1952), and in British patent specification GB 1 514 907. Phenylguanidines which are substituted on the aromatic ring have higher melting points than unsubstituted analogs and therefore can be isolated as free bases or sometimes as their hydrochlorides, which precipitate from aqueous solution which makes them unsuitable for the present invention.

As a free base, phenylguanidine is highly watersoluble and hygroscopic, and absorbs carbon dioxide from the air. It is therefore desirable to isolate the phenylguanidine as a salt, for example as its carbonate or hydrogencarbonate, in order to enhance its stability on storage. It is further desirable to reduce the amount of waste water of the known process and to increase the yield and purity of the isolated salt.

Surprisingly it has now been found that by conducting the process within a specified pH-range and using controlled addition of hydrochloric acid, a substantial increase in yield is observed and negligible amounts of side products are produced.

The advantages of the process presently described include the following: a higher yield is achieved while the reaction time is reduced; precipitation of the crystalline carbonate or hydrogencarbonate occurs at elevated temperatures without thermal decomposition; highly pure crystalline product is formed which filters easily; no activated carbon is used thereby simplifying product isolation; a much reduced waste water volume is found, leading to a more economic and ecologically acceptable process.

The process according to the present invention is for the production of phenylguanidine carbonate or hydrogencarbonate from aniline, hydrochloric acid, cyanamide and an alkali metal carbonate or hydrogencarbonate, which comprises a) mixing 1 mole equivalent of aniline with such an amount of an aqueous solution of 10 to 37% by weight hydrochloric acid, at a temperature from 20° to 105° C., that the resulting aniline hydrochloride solution has a pH value of 2.0 to 4.0;

b) adding 1 to 1.5 mole equivalents of aqueous cyanamide solution to the stirred reaction mixture from a) while adjusting the reaction temperature to between 60° and 105° C., and maintaining the pH in the region 2.0 to 4.0 by further addition of aqueous hydrochloric acid solution, and allowing the reaction to run to completion; and c) cooling the reaction mixture to 20° to 90° C., and combining the mixture with 1 to 2 mole equivalents of alkali metal hydrogen carbonate or 0.5 to 1 mole equivalent alkali metal carbonate in solid form or as an aqueous solution or a suspension in water, resulting in a crystalline precipitate of phenylguanidine hydrogencarbonate or carbonate.

The preferred concentration of the aqueous solution of hydrochloric acid is from 20 to 36% by weight.

The pH is preferably maintained in steps a) and b) at 2.0 to 3.0.

The reaction temperature for stage a) is preferably 60° to 105° C., and more preferably 80° to 95° C.

The reaction temperature for stage b) is preferably 80° to 95° C.

The reaction temperature for stage c) is preferably from 40° to 80° C.

The alkali metal hydrogencarbonate may be LiHCO$_3$, NaHCO$_3$ or KHCO$_3$, preferably NaHCO$_3$.

The alkali metal carbonate may be Li$_2$CO$_3$, Na$_2$CO$_3$ or K$_2$CO$_3$, preferably Na$_2$CO$_3$.

The alkali metal hydrogen carbonate or carbonate is preferably used in stage c) in the form of an aqueous solution or a suspension in water.

The reaction time for each of stages a) and b) may vary from 10 minutes to 5 hours, though the preferred range is 2 to 4 hours, depending on the quantities and conditions employed. The product can be isolated easily by known methods such as filtration or centrifugation and decantation, and can be produced in a hydrated or dehydrated form, depending on the drying conditions.

The following Examples illustrate the process according to the invention.

EXAMPLE 1

88.5 g (0.78 mol) aqueous HCl (32% by weight) are added to 93.1 g aniline (1.0 mol) until the pH value reaches 2.0. Over the course of 1 hour, 92.4 g (1.1 mol) of a 50% aqueous cyanamide solution are run into the reaction mixture at 85° C. Towards the end of the cyanamide addition, a further 22.1 g (0.19 mol) aqueous HCl (32%) are added, which returns the pH to 2.4 to 2.7. After stirring for 2 hours at 85° C., the mixture is allowed to cool to 60° C. and a solution of 63.6 g (0.6 mol) sodium carbonate in 170 ml water is added over a 30 minute period. The crystalline precipitate is filtered after cooling to 5° C. 163 g phenylguanidine carbonate are produced, containing 76.7% phenylguanidine free base, which corresponds to a 92.7% yield based on aniline. The melting point (decomposition) is 147° to 150° C.

EXAMPLE 2

The procedure of Example 1 is repeated using the same quantities, but the reaction mixture is added to the sodium carbonate solution at 50° C. 165 g phenylguanidine carbonate (76.7% free base) are produced, equivalent to a 93.7% yield. The melting point (decomposition) is 147° to 150° C.

EXAMPLE 3

To 98.2 g aniline (1.0 mol) is added 32% HCl until the pH of the solution reaches approximately 2.5; 95.2 g (0.83 mol) 32% HCl are required. The solution is heated to 87° C. and stirred while 93.0 g of a 50% aqueous solution of cyanamide (1.10 mol) are added over a period of 1 hour. Shortly before completion of the cyanamide addition, another 16.8 g (0.15 mol) 32% HCl are added. After 3 hours stirring at 87° C. the solution is cooled to 60° C. and added to a stirred suspension of 101.0 g (1.20 mol) sodium hydrogencarbonate in 170 ml water at 60° C. After cooling to 5° C., 127.6 g phenylguanidine hydrogencarbonate (dried at 45° C./100 mbar) are isolated (66.8% free base), representing a yield of 94.5% based on aniline. The melting point (decomposition) is 150° to 152° C.

EXAMPLE 4

A solution of 77 kg aniline (827 mol) and 81 kg 32% HCl (710 mol) is prepared having a pH value of 2.6; the solution is heated to 85° to 90° C. and stirred for 2 hours during which time 76 kg of 50% aqueous cyanamide solution (905 mol) are added. Shortly before completion of the cyanamide addition, the pH value is returned to between 2 and 3 by addition of 32% HCl portions, 12 kg HCl solution in total. After 3 hours stirring, the solution is cooled to 60° C. and at this temperature there is added a solution of 53 kg sodium carbonate (500 mol) in 150 l water. Upon cooling to 20° C. the crystalline precipitate is separated by filtration and washed twice with 130 l water (the filtrate of the second wash is used for the first wash in the next batch). After drying at 70° C./30 mbar, 136 kg light beige crystals of phenylguanidine carbonate are obtained (77.4% free base), representing a yield of 94.3% based on aniline. The melting point (decomposition) is 147° to 150° C.

EXAMPLE 5

Preparation of Phenylguanidine Hydrogencarbonate According to the Trostberg Procedure.

114.1 g HCl (32%) are stirred into a mixture of 98.2 g (1.0 mol) aniline (94.8%, water 5%) and 84 g water which is cooled externally with cold water. The reaction mixture is heated to boiling and 104.6 g (1.25 mol) cyanamide (50%) stirred into the boiling solution over a period of 30 minutes. The mixture is refluxed for 2 hours after which 4.8 g activated carbon are added carefully. The activated carbon residue is removed by filtration at 60° C. The filtered aqueous solution of 1-phenylguanidinium chloride is added to a stirred suspension of 130.2 g (1.53 mol) sodium bicarbonate in 0.5 l water. The mixture is stirred for four hours. The precipitated phenylguanidine hydrogencarbonate is separated by filtration, suspended in 0.43 l water and stirred intensively for 1 hour. After filtration the product is again suspended in 0.32 l water, stirred intensively for one hour and separated by filtration. The reaction product is dried at 50° C. under vacuum.

Precipitation is observed from the reaction solution at 80° C. 144 g colourless phenylguanidine hydrogencarbonate are isolated (67.3% free base), representing a 72.2% yield based on aniline. The decomposition temperature is 150° to 153° C. The side products phenylurea and diphenylurea are produced in amounts 0.5 and 0.2% yield respectively.

EXAMPLE 6

Example 5 is repeated but under the process conditions according to the invention.

169.1 g phenylguanidine hydrogencarbonate are isolated (68.0% free base), representing a yield of 85.1% based on aniline. No side products are identified and no precipitation is observed at 80° C.

It should be noted that the aniline quality used in Examples 5 and 6 is identical, and is different from that used in Examples 1 to 4.

I claim:

1. A process for the production of phenylguanidine carbonate or hydrogencarbonate from aniline, hydrochloric acid, cyanamide and an alkali metal carbonate or hydrogencarbonate, which comprises
   a) mixing 1 mole equivalent of aniline with such an amount of an aqueous solution of 10 to 37% by weight hydrochloric acid, at a temperature from 20° to 105° C., that the resulting aniline hydrochloride solution has a pH value of 2.0 to 4.0;
   b) adding 1 to 1.5 mole equivalents of aqueous cyanamide solution to the stirred reaction mixture from a) while adjusting the reaction temperature to between 60° and 105° C., and maintaining the pH in the region 2.0 to 4.0 by further addition of aqueous hydrochloric acid solution, and allowing the reaction to run to completion; and
   c) cooling the reaction mixture to 20° to 90° C., and combining the mixture with 1 to 2 mole equivalents of alkali metal hydrogen carbonate or 0.5 to 1 mole equivalent alkali metal carbonate in solid form or as an aqueous solution or a suspension in water, resulting in a crystalline precipitate of phenylguanidine hydrogencarbonate or carbonate.

2. A process according to claim 1, wherein the concentration of the aqueous solution of hydrochloric acid is from 20 to 36% by weight.

3. A process according to claim 1, wherein the pH is maintained in steps a) and b) at 2.0 to 3.0.

4. A process according to claim 1, wherein the reaction temperature for stage a) is 60° to 105° C.

5. A process according to claim 4, wherein the reaction temperature for stage a) is 80° to 95° C.

6. A process according to claim 1, wherein the reaction temperature for stage b) is 80° to 95° C.

7. A process according to claim 1, wherein the reaction temperature for stage c) is from 40° to 80° C.

8. A process according to claim 1, wherein the alkali metal hydrogencarbonate is $LiHCO_3$, $NaHCO_3$ or $KHCO_3$.

9. A process according to claim 8, wherein the alkali metal hydrogencarbonate is $NaHCO_3$.

10. A process according to claim 1, wherein the alkali metal carbonate is $Li_2CO_3$, $Na_2CO_3$ or $K_2CO_3$.

11. A process according to claim 10, wherein the alkali metal carbonate is $Na_2CO_3$.

12. A process according to claim 1, wherein the alkali metal hydrogen carbonate or carbonate is used in stage c) in the form of an aqueous solution or a suspension in water.

* * * * *